US006884239B2

United States Patent
Houzego et al.

(10) Patent No.: US 6,884,239 B2
(45) Date of Patent: Apr. 26, 2005

(54) INGESTIBLE DEVICE FOR THE RELEASE OF SUBSTANCES AT DISTINCT LOCATIONS IN ALIMENTARY CANAL

(75) Inventors: Peter John Houzego, Cambridge (GB); Peter Neil Morgan, Cambridge (GB); Peter Hanson Hirst, Nottinghamshire (GB); Duncan James Westland, Cambridge (GB); Ian Robert Wilding, Nottingham (GB)

(73) Assignee: Phaeton Research Limited, Nottingham (GB)

( * ) Notice: Subject to any disclaimer, the term of this patent is extended or adjusted under 35 U.S.C. 154(b) by 485 days.

(21) Appl. No.: 10/176,160

(22) Filed: Jun. 20, 2002

(65) Prior Publication Data

US 2004/0215171 A1 Oct. 28, 2004

Related U.S. Application Data

(63) Continuation of application No. PCT/GB00/04913, filed on Dec. 20, 2000.

(30) Foreign Application Priority Data

Dec. 20, 2000 (GB) .............................................. 9930001

(51) Int. Cl.[7] ....................... A61M 31/00; A61M 37/00; A61M 36/00; A61K 9/22; A61N 5/00
(52) U.S. Cl. ............................... 604/890.1; 604/93.01; 600/7
(58) Field of Search ............................. 604/20, 93.01, 604/113, 890.1, 892.1; 600/2, 3, 7

(56) References Cited

U.S. PATENT DOCUMENTS

| | | | |
|---|---|---|---|
| 4,239,040 A | 12/1980 | Hosoya et al. | |
| 4,425,117 A | 1/1984 | Hugemann et al. | |
| 4,507,115 A | 3/1985 | Kambara et al. | |
| 5,279,607 A | 1/1994 | Schentag et al. | |
| 6,632,216 B1 * | 10/2003 | Houzego et al. | 604/890.1 |

FOREIGN PATENT DOCUMENTS

EP          0 715 847 A2     6/1996

OTHER PUBLICATIONS

Lambert, et al., "Autonomous telemetric capsule to explore the small bowel," *Medical & Biological Engineering & Computing* 29(2):191–196 (1991).

* cited by examiner

*Primary Examiner*—Nicholas Lucchesi
*Assistant Examiner*—Mark K. Han
(74) *Attorney, Agent, or Firm*—Pabst Patent Group LLP

(57) ABSTRACT

The field of the invention is site-specific drug delivery capsules (SSDC's). The disclosure relates to a closure member (14) for a substance reservoir (12) of an SSDC (10). The SSDC (10) includes a retainer that provides a non-linear force resisting opening of the closure member (14). The non-linear force ensures that the closure member (14) unseals the reservoir (12) only when an opening force exceeds a maximal value of the resisting force, thereby preventing premature or accidental emptying of the reservoir (12). The preferred means of providing the resistive force is a rolling, elastomeric o-ring (64) that additionally seals the closure member (14) into an aperture (13).

19 Claims, 4 Drawing Sheets

INGESTIBLE DEVICE FOR THE RELEASE OF SUBSTANCES AT DISTINCT LOCATIONS IN ALIMENTARY CANAL

This application is a continuation of International Application No. PCT/GB00/04913 entitled "Ingestible Device for the Release of Substances at District Locations in Alimentary Canal", filed in the United Kingdom Receiving Office for the PCT on Dec. 20, 2000, which claims priority to British application Serial No. 9930001.4, filed Dec. 21, 1999.

This invention relates to an ingestible device. In particular the invention relates to such a device in the form of a capsule that is intended to release a controlled quantity of a substance, such as a pharmaceutically active compound, foodstuff, dye, radiolabelled marker, vaccine, physiological marker or diagnostic agent at a chosen location in the gastrointestinal (GI) tract of a mammal. Such a capsule is sometimes referred to as a "Site-Specific Delivery Capsule", or SSDC.

SSDC's have numerous uses. One use of particular interest to the pharmaceutical industry involves assessing the absorption rate and/or efficacy of a compound under investigation, at various locations in the GI tract. Pharmaceutical companies can use data obtained from such investigations, eg. to improve commercially produced products.

Several designs of SSDC are known. One design of capsule intended for use in the GI tract of a mammal is disclosed in "Autonomous Telemetric Capsule to Explore the Small Bowel", Lambert et al, Medical & Biological Engineering and Computing, March 1991. The capsule shown therein exhibits several features usually found in such devices, namely:
- a reservoir for a substance to be discharged into the GI tract;
- an on-board energy source;
- a mechanism, operable under power from the energy source, for initiating discharge of the substance from the reservoir;
- a switch, operable remotely from outside the body of the mammal, for initiating the discharge; and
- a telemetry device for transmitting data indicative of the status, location and/or orientation of the capsule.

Also, of course, the dimensions of the capsule are such as to permit its ingestion via the oesophagus; and the external components of the capsule are such as to be biocompatible for the residence time of the capsule within the body.

The capsule disclosed by Lambert et al suffers several disadvantages. One disadvantage is the complexity of the device. This means that the capsule is expensive to manufacture. Also the complexity means that the capsule is prone to malfunction.

Additionally the capsule disclosed by Lambert et al includes a resiliently deformable dosing chamber that is opened when desired to expel a substance into the GI tract. The dosing chamber is difficult to fill and seal before use.

Some other designs of SSDC operate by simply opening an aperture in the wall of the substance reservoir (dosing chamber), whereby the substance may diffuse into the GI tract. This method of discharging the substance is inefficient because:
(i) the duration of the discharge is too long, whereby substance concentrations in localised areas of the GI tract may be lower than intended by users of the SSDC;
(ii) the time taken to discharge the substance may lead to the SSDC departing a preferred site in the GI tract before discharge is complete; and
(iii) some of the substance may remain indefinitely lodged in the reservoir.

As a solution to this problem U.S. Pat. No. 4,425,117 discloses an SSDC in which a powered piston simultaneously opens the reservoir and expels the substance therefrom. This design is believed to be prone to leakage of the substance.

U.S. Pat. No. 5,279,607 also discloses an SSDC having a pressurisable reservoir, but the overall arrangement of this device is complicated. The sealing of the aperture against leakage and premature opening is not addressed in detail, so it is believed that U.S. Pat. No. 5,279,607 also fails to disclose a device satisfying the multiple requirements of:
- good pre-dosing sealing of the reservoir;
- reliable opening of the reservoir;
- positive expulsion of the substance from the reservoir at the appropriate time; and
- simplicity of construction and use.

According to a first aspect of the invention, there is provided a device as defined in Claim 1.

The use of a retainer, for the closure member, that provides limited resistance to movement thereof, and that permits full movement thereof once the force on the member attains a threshold value, allows the device of the invention to survive perturbations and electromagnetic noise that might cause premature leaking of the reservoirs of the prior art SSDC's; while permitting positive opening of the reservoir when required.

Further, advantageous features of the invention are set out in the claims depending from Claim 1.

The features of Claim 2 advantageously permit the forced expulsion of the substance from the reservoir.

More preferably the resistance provided by the retainer is as defined in claim 3. This ensures that, when the force on the closure member is less than a minimum, the closure member does not move; and that when the force exceeds the minimum the closure member only moves sufficiently to unseal the aperture if the force attains the threshold value.

Preferably the retainer arrangement is as defined in claim 5. In preferred embodiments the o-ring is compressed as defined in Claims 6 and 7, in order to provide one source of a constant force as defined in Claim 3. The use of an o-ring ensures that the closure member seals effectively into the reservoir aperture. Consequently the closure member of the invention may be used both for filling and emptying of the reservoir, obviating the need for a separate filling orifice and mechanism and thereby simplifying the SSDC.

The preferred action of the o-ring involves the o-ring turning itself inside out while moving in a groove, as defined in Claims 8 and 9. This arrangement conveniently provides the varying force defined in Claim 3.

A particularly preferred form of the o-ring has a circular transverse cross section.

The groove and apart of the exit aperture may include ribs, as defined in Claims 11 and 12, that advantageously encourage rolling of the o-ring and reduce the tendency of the o-ring to slide relative to the bung and exit aperture when the closure member experiences a force. The ribs also promote effective sealing.

Claims 13 to 18 define advantageous features of the structure of the device.

There now follows a description of preferred embodiments of the invention, by way of non-limiting example, with reference being made to the accompanying drawings in which.

Figure 1:
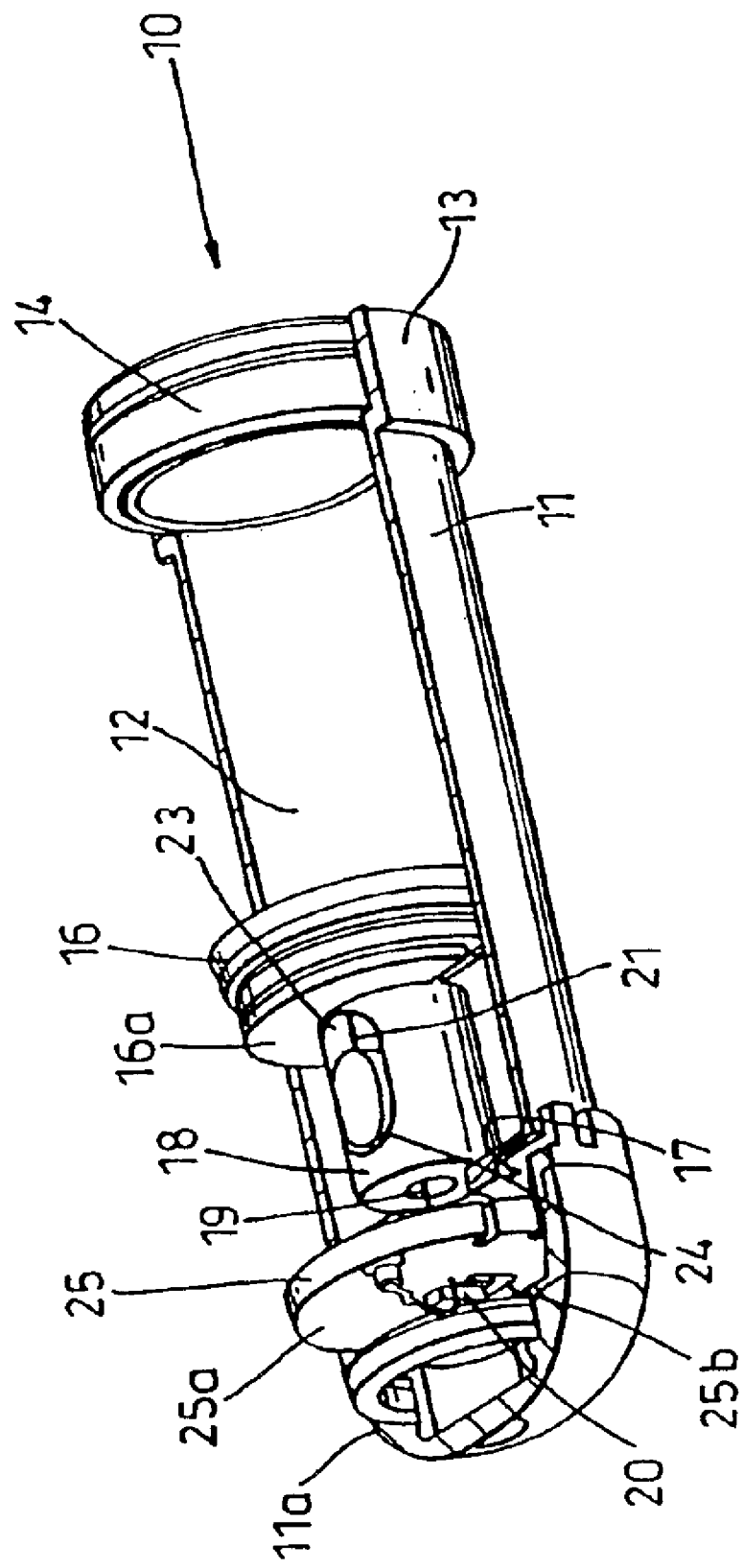
FIG. 1 shows in perspective, partly sectioned view a device according to the invention.

Referring to the drawings there is shown an ingestible device 10 according to the invention.

The overall envelope of the device 10 has been designed to be compatible with swallowing and smooth passage through the GI tract. To support this requirement the outer housing 11 of device 10 is smooth with no sharp edges and preferably has at least one end rounded as shown at 11a to facilitate swallowing. The diameter of the capsule preferably does not exceed 12 mm and the length preferably does not exceed 35 mm. The precise dimensions represent an optimisation between overall capsule size and the volume of a drug containing reservoir 12. In a preferred embodiment of the invention for a drug volume of 1 ml the reservoir 12 has a diameter of 11 mm and length 32 mm. The rounded end 11a can within the scope of the invention range between a hemispherical profile and a flat end with a 2 mm radius corner.

The structure and operation of device 10 are, in simple terms, as follows:

Reservoir 12 has a cylindrical interior and is open at one end 13 located at the opposite end of device 10 to rounded end 11a. Before use of the device 10 reservoir 12 is filled with a substance via aperture (open end) 13. Aperture 13 of reservoir 12 is then sealed against leakage of the contents of the hollow interior of reservoir by a closure member in the form of bung 14. Bung 14 is removable from aperture 13, in a manner described below, to permit expulsion of the contents (which may be in liquid, powder or even solid form) from the interior of reservoir 12.

The removal of bung 14, in use of the apparatus in the GI tract of a mammal, from aperture 13 is by virtue of selectively controlled pressurising of the interior of reservoir 12.

This is achieved through the action of an actuator mechanism in the form of a cylindrical piston 16 that is sealingly slideable along the interior of reservoir 12 under power from an energy source (eg. a stored energy device that is, for clarity, omitted from FIG. 1).

The interior of device 10 on the side of piston 16 remote from reservoir 12 is generally hollow. Thus the energy source may in preferred embodiments take the form of a compressed spring whose spring force acts between eg. the rear face of piston 16 and a shoulder defined by an annular or part-annular rib 17 that is integral with and hence fixed relative to the housing 11.

The device 10 includes a releasable latch that operates to latch the energy source in a potential energy state until a chosen time.

In the FIG. 1 embodiment the latch is in the form of an anchor 18, secured relative to piston 16, for a thread 19 made of or at least including a sharp melting point material; and a heater 20 whose function is to heat the sharp melting point thread and melt it or at least cause a dramatic increase in its ductility at a chosen time.

More specifically, in the preferred embodiment anchor 18 includes a tubular sleeve 21 one end face of which is rigidly secured to the rear face 16a of piston 16, such that the elongate axis of sleeve 21 is generally perpendicular to rear face 16a.

The hollow interior of sleeve 21 opens at the end of sleeve 21 remote from piston 16.

Sleeve 21 includes an elongate perforation 23, whose elongate axis is generally parallel to the elongate axis of sleeve 21, passing through the wall of sleeve 21 as shown. A similar perforation passes through the wall of sleeve 21 on the opposite side thereof.

An elongate cylindrical anchor member 24 is slideably received at either end in the respective perforations, whereby the elongate axis of the anchor member is generally perpendicular to the elongate axis of the sleeve 21.

The diameter of anchor member 24 is less than the width of each perforation, whereby anchor member may be slid into place as shown, during assembly of device 10.

Anchor member 24 has firmly secured thereto one end of thread 19. Thread 19 passes through the hollow interior of sleeve 21 and emerges at the free end thereof, from where it passes through an aperture 25b in a printed circuit board (pcb) 25. Pcb25 is in the form of a disc secured against the side of annular rib 17 remote from reservoir 12. Thread 19 is firmly secured to the surface 25a of pcb that is remote from reservoir 12. Surface 25a also mounts heater 20 in the form of a resistor. Thread 19 passes over heater 20 between the aperture and the attachment point of thread 19 to the pcb 25a.

If as disclosed hereinabove a compression spring (not shown in FIG. 1) acts between the rib 17 and piston 16, on assembly of device 10, sleeve 21 will be forced, by virtue of its attachment to piston 16, towards reservoir 12 until anchor member 18 engages the end of each perforation 23 remote from piston 16, causing thread 19 to become taut and thereby preventing the further travel of piston 16 towards bung 14 while thread 19 is intact. The tension in thread 19 draws pcb 25 hard against rib 17, thereby optionally obviating the need for further restraint of pcb 25.

Pcb 25 includes a tuned receiver of externally applied radiation whereby on the device passing through an electromagnetic field of the frequency to which the receiver is tuned, a current is induced that is fed to resistor heater 20. The heat from the heater 20 melts or renders highly ductile the thread 19, whereby piston 16 becomes free to move towards bung 14 powered by the energy stored in the spring.

Figure 2:
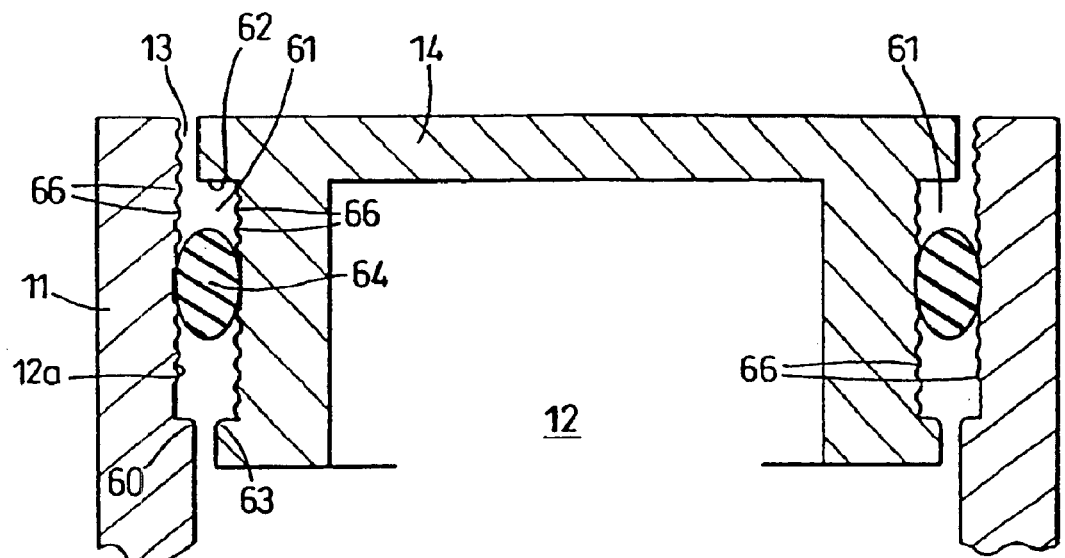
FIG. 2 shows in cross-sectional view the closure member and exit aperture of the FIG. 1 device in a sealed condition.
Figure 3:
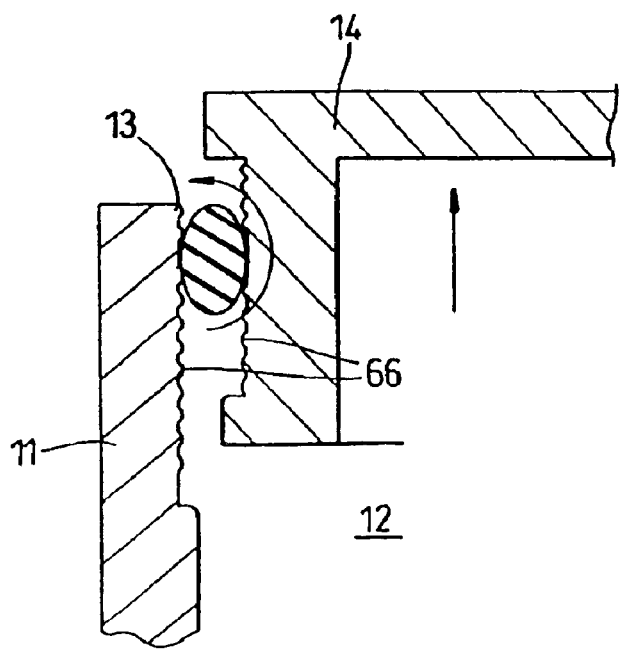
FIG. 3 shows the FIG. 2 components part way through an unsealing operation.
Figure 4:
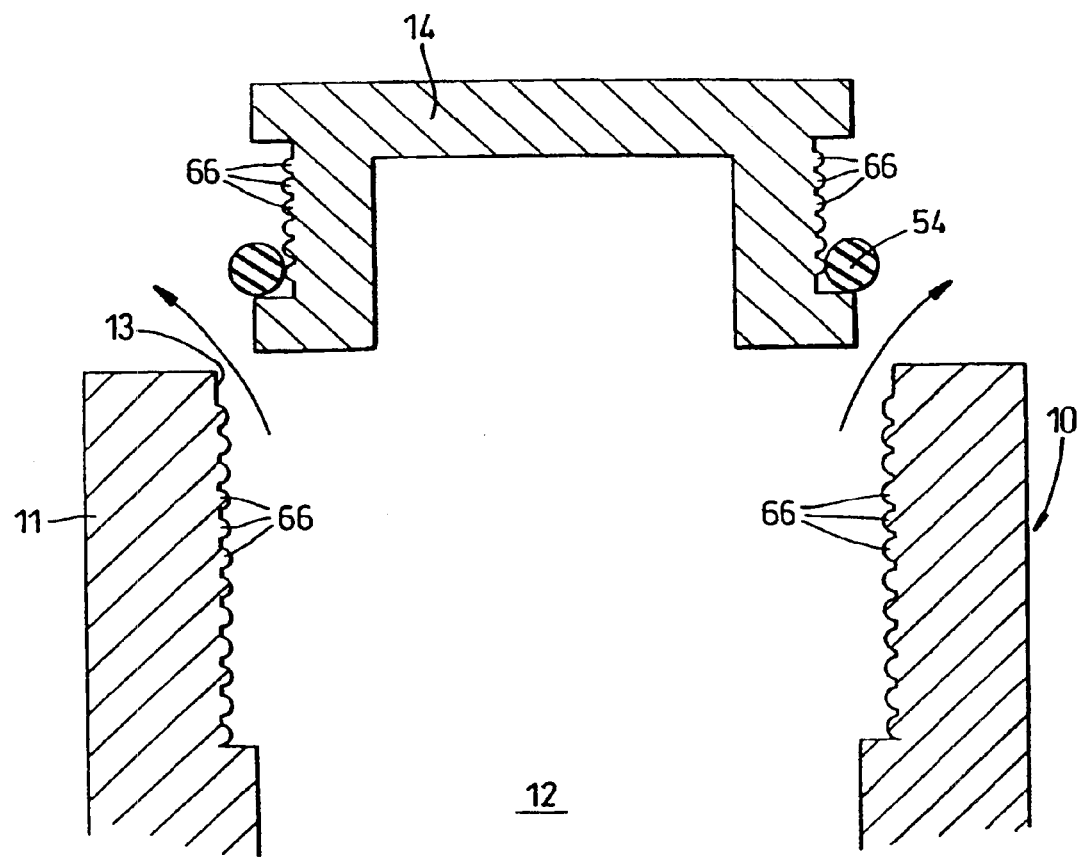
FIG. 4 shows the FIG. 2 components in an unsealed condition.

Referring now to FIGS. 2 to 4, the bung 14 and exit aperture 13 are shown in more detail.

Exit aperture 13 is defined by a terminal portion of reservoir 12 that defines, in the region of aperture 13, a hollow cylindrical interior 12a.

Spaced a short distance from aperture 13, the hollow cylindrical interior 12a defines a radially inwardly projecting shoulder 60.

Bung 14 is a generally cylindrical member the outer, cylindrical wall 14a of which has formed therein an axially extending groove or trough 61.

At either axial end, groove 61 terminates in a radially outwardly projecting shoulder 62, 63.

An endless elastomeric (resiliently deformable) o-ring 64 encircles bung 14 in the vicinity of groove 61. The unstretched diameter of the annulus of o-ring 64 is such that the o-ring will not naturally pass over either shoulder 62, 63, even when bung 14 is separated from device 10. Thus o-ring 64 is retained in groove 61 by its elasticity.

The diameter of bung 14 in the vicinity of each shoulder 62, 63 is such that the bung 14 is a sliding fit in the vicinity of cylindrical interior 12a.

Thus the diameter of shoulder 63 is slightly less than that of shoulder 60, for example.

The diameter of groove 61 and the cylindrical interior 12a are such that, on insertion of bung 14 into interior 12a, the member defining o-ring 61 is compressed to 50%–80% of its uncompressed diameter, along its entire length. This ensures a good seal of the bung 14 into aperture 13, and also provides a component of a resistive force as detailed hereinbelow.

The wall of cylindrical interior 12a and the base of groove 61 each have formed therein a series of upstanding cicumferential ridges or ribs 66. The ribs 66 promote rolling, as opposed to sliding, of o-ring 64 along hollow interior 12a and groove 61, as bung 14 moves in aperture 13 relative to hollow interior 12a.

The ribs 66 also enhance the sealing of the exit aperture 13 by the o-ring 64.

When the bung 14 experiences a force tending to move it axially relative to the device 10, the o-ring therefore tends to roll. If the force drives the bung into the reservoir 12, the o-ring abuts shoulder 60 after a short travel and prevents further movement of bung 14.

If the force on bung 14 is generated by the actuator mechanism (ie. piston 16) it tends to drive bung 14 out of reservoir 12, simultaneously causing rolling of o-ring 61.

Rolling of a compressed elastomeric circular section such as an o-ring generates two components of force that resist rolling, namely:

(i) the force arising from deformation of the o-ring as it rolls. This force is zero initially and rises to a substantially constant value; and (ii) the force arising from turning inside out of the o-ring as the inside diameter rolls around to become the outer diameter. This requires stretching and compression respectively of the inner and outer sections of the o-ring.

Figure 5:
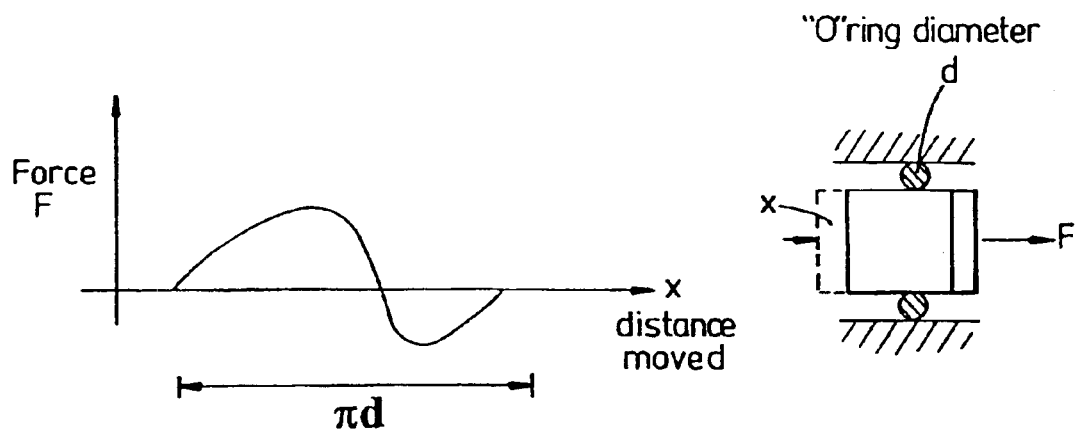
FIG. 5 is a graph of the resistive force arising from rolling of an elastomeric o-ring, plotted against distance rolled.

The force (ii) is non-uniform and is related to the diameter of the o-ring section, as shown in FIG. 5, which plots the resistive force due to turning inside out of the o-ring against the distance rolled.

Figure 6:
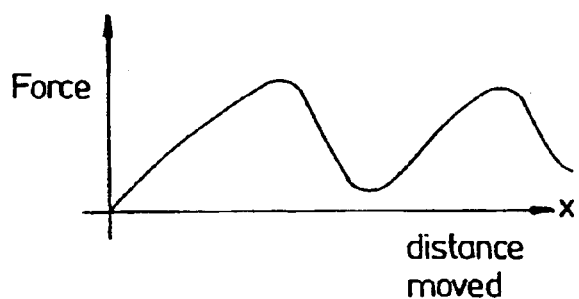
FIG. 6 is a graph of the total resistive force arising from rolling of a compressed elastomeric o-ring, plotted against distance rolled.

The sum of the forces (i) and (ii) is similarly plotted in FIG. 6. It will thus be apparent that the compressed o-ring acts as a retainer for the bung 14 whose resistance to motion is the sum of a generally constant force and a force whose magnitude varies in dependence on the position of the bung 14 relative to the exit aperture 13. Clearly a force exceeding force (i) discussed hereinabove will cause limited movement of the bung, but as shown by FIG. 6 the total resistive force increases to a maximum (ie. the threshold value) as the o-ring starts to roll inside out.

The diameter of the o-ring, the length of the groove 61 and the length of cylindrical interior 12a are chosen such that when the bung experiences a force driving it out of aperture 13 in the length of cylindrical interior 12a o-ring 64 has room to turn completely inside out no more than once before the bung 14 emerges from aperture 13 as shown in FIG. 4.

Since as shown by FIG. 6 the resistive force ((i)+(ii)) decreases from its maximum with further rolling of the o-ring 64 beyond the point corresponding to the peak force, the chosen dimensions of the components ensure that the bung 14 is expelled from aperture 13 as long as the force acting on bung 14 continuously exceeds the value of component (i) of the resistive force, by a comparatively small amount, after the o-ring has turned inside out. In other words, the action of the o-ring replicates an "over centre" force resisting and then readily permitting expulsion of the bung 14.

Although the closure shown in FIGS. 2 to 4 could be used in a variety of different types of SSDC, its use in an SSDC as shown in FIG. 1 is preferred because of the presence of a positive displacement piston 16. Piston 16 ensures that the force acting on bung 14 exceeds resistive force component (i) at all times once opening of the reservoir has been triggered.

FIG. 4 shows the condition of the parts of the device 10 after release of bung 14. O-ring has reverted to a generally circular cross-section. It is retained by its resilience encircling bung 14 that is recoverable in the stools of the mammal separately from the remainder of device 10. The expulsion of the substance, under pressure, from reservoir 12 is indicated schematically by the arrows in FIG. 4.

What is claimed is:

1. An ingestible device for delivering a substance to a chosen or identifiable location in the alimentary canal of a human or animal, comprising:

an openable reservoir, for the substance, that is sealable against leakage of the substance, the reservoir including an exit aperture, for the substance, closeable by a closure member releasably sealed to the aperture;

an actuator mechanism for opening the reservoir;

an energy source, operatively connected for powering the actuator mechanism;

a releasable latch for controllably switching the application of power to the actuator from the energy source; and a receiver of electromagnetic radiation for operating the latch when the receiver detects radiation within a predetermined characteristic range, wherein the actuator mechanism operates by applying a force to the closure member, characterized in that the device includes a retainer member, for the closure member, that provides limited resistance to unsealing of the closure member from the exit aperture whereby, on the said force on the closure member attaining a threshold value, the said resistance is overcome and the closure member unseals the exit aperture to permit discharge of the substance from the reservoir.

2. A device according to claim 1 wherein the actuator mechanism operates by pressurizing the substance in the reservoir to apply the force to the closure member, whereby on unsealing of the exit aperture the substance is expelled from the reservoir under pressure.

3. A device according to claim 1 or 2 wherein the resistance provided by the retainer member is the sum of a generally constant force and a force whose magnitude varies in dependence on the position of the closure member relative to the exit aperture.

4. A device according to any preceding claim wherein the retainer member includes a resiliently deformable member interconnecting the closure member and a part of the device fixed relative to the exit aperture, whereby the said resistance acts directly or indirectly between the closure member and the exit aperture.

5. A device according to any preceding claim wherein the exit aperture is defined by a hollow, cylindrical portion of the reservoir and the closure member is a generally cylindrical bung that is moveably receivable in the exit aperture, the cylindrical outer side wall of the bung including a peripheral groove, the retainer member including a resiliently deformable o-ring seated in the said groove and sealingly interconnecting the peripheral groove and the hollow, cylindrical portion whereby on movement of the bung relative to the exit aperture the o-ring moves relative to at least one of the groove and the hollow, cylindrical portion.

6. A device according to claim 5 wherein the o-ring is compressed between the peripheral groove and the hollow cylindrical portion, thereby causing a generally constant force resisting movement of the bung relative to the exit aperture, on rolling of the o-ring relative to the said grooves and hollow cylindrical portion.

7. A device according to claim 6 wherein the o-ring is compressed to between about 50% to about 80% of its uncompressed thickness.

8. A device according to any of claim 5 to 7 wherein the width of the grooves and the axial length of the hollow, cylindrical portion are such that, on the bung moving more than a predetermined distance relative to the exit aperture, in a direction tending to open the exit aperture, the o-ring rolls and turns inside out along its entire circumference, thereby causing a force, resisting movement of the bung relative to the exit aperture, whose magnitude increases to a maximal value and decreases as the bung moves the said predetermined distance.

9. A device according to claim 8 wherein the cross-section of the o-ring, the axial length of the hollow, cylindrical portion and the width of the groove are such that, on the bung moving more than the said predetermined distance in the said direction, the bung opens the exit aperture before the o-ring again turns inside out, thereby providing a single force threshold resisting opening of the exit aperture.

10. A device according to claim 5 or any claim dependent therefrom, wherein the o-ring is circular in transverse cross-section.

11. A device according to claim 5 or any claim dependent therefrom, wherein the peripheral groove includes upstanding from the base thereof a series of annular ribs extending generally parallel to the said base.

12. A device according to claim 5 or any claim dependent therefrom, wherein the hollow, cylindrical portion includes a series of annular ribs extending radially inwardly from the wall of the hollow, cylindrical portion.

13. A device according to claim 5 or any claim dependent therefrom, wherein the hollow cylindrical portion terminates at one end in the exit aperture and at an opposite end in a shoulder that protrudes into the hollow, cylindrical portion to limit movement of the bung in a direction towards the reservoir.

14. A device according to claim 5 or any claim dependent therefrom, wherein on opening of the exit aperture the bung separates from the device.

15. A device according to claim 5 or any claim dependent therefrom wherein the o-ring is captive relative to the bung.

16. A device according to any preceding claim including a transmitter operable to transmit a signal indicative of opening of the exit aperture for release of the substance from the reservoir.

17. A device according to any preceding claim wherein the reservoir includes a hollow, elongate cylinder and the actuator mechanism includes a piston moveable in the cylinder under power from the energy source to pressurize the reservoir thereby opening the closure member and expelling the substance from the reservoir.

18. A device according to any preceding claim wherein the reservoir contains a charge of a liquid, powdered or solid substance, or a suspension or a solution.

19. A device according to claim 18 wherein the reservoir has been filled via the exit aperture before closing of the exit aperture by the closure member.

* * * * *

UNITED STATES PATENT AND TRADEMARK OFFICE
CERTIFICATE OF CORRECTION

PATENT NO. : 6,884,239 B2
APPLICATION NO. : 10/176160
DATED : April 26, 2005
INVENTOR(S) : Peter John Houzego et al.

It is certified that error appears in the above-identified patent and that said Letters Patent is hereby corrected as shown below:

Claim 1, column 6, line 31, insert --; and in that the retainer member includes a resiliently deformable member interconnecting the closure member and a part of the device fixed relative to the exit aperture, whereby the said resistance acts directly or indirectly between the closure member and the exit aperture, the resiliently deformable member including an elastomeric o-ring that is retained in a groove and that interconnects the closure member and the exit aperture whereby on movement of the closure member relative to the exit aperture the o-ring moves relative to at least the exit aperture or the groove.-- after reservoir.
Claim 3, column 6, line 37, delete "or 2".
Claim 4, column 6, lines 42 to 46, delete entire claim.
Claim 5, column 6, line 47, replace "any preceding claim" with --claim 1--.
Claim 5, column 6, line 52, replace "a peripheral" with --the said--.
Claim 5, column 6, line 52, insert --that extends peripherally-- after groove.
Claim 5, column 6, line 53, delete "seated in the said groove and".
Claim 5, column 6, line 57, replace "and" with --or--.
Claim 8, column 7, line 1, replace "any of claim 5 to 7" with --claim 5--.
Claim 10, column 7, lines 18 and 19, delete "any claim dependent therefrom".
Claim 11, column 7, lines 21 and 22, delete "any claim dependent therefrom".
Claim 12, column 7, lines 25 and 26, delete "any claim dependent therefrom".
Claim 13, column 8, lines 1 and 2, delete "any claim dependent therefrom".
Claim 14, column 8, lines 7 and 8, delete "any claim dependent therefrom".
Claim 15, column 8, lines 10 and 11, delete "any claim dependent therefrom".
Claim 16, column 8, line 12, replace "any preceding claim" with --claim 1--.
Claim 17, column 8, line 16, replace "any preceding claim" with --claim 1--.
Claim 17, column 8, line 22, replace "any preceding claim" with --claim 1--.

Signed and Sealed this

Twenty-fifth Day of March, 2008

JON W. DUDAS
*Director of the United States Patent and Trademark Office*